United States Patent [19]

Hall et al.

[11] 4,159,278
[45] Jun. 26, 1979

[54] DIOXAMIC ACIDS AND SALTS

[75] Inventors: Charles M. Hall; John B. Wright, both of Kalamazoo, Mich.

[73] Assignee: The Upjohn Company, Kalamazoo, Mich.

[21] Appl. No.: 847,189

[22] Filed: Oct. 31, 1977

Related U.S. Application Data

[60] Continuation of Ser. No. 714,571, Aug. 16, 1976, abandoned, which is a division of Ser. No. 382,762, Jul. 26, 1973, Pat. No. 3,993,679, which is a continuation-in-part of Ser. No. 317,005, Dec. 20, 1972, abandoned.

[51] Int. Cl.$^2$ .............................................. C07C 91/26
[52] U.S. Cl. .............................. 260/501.15; 562/433; 562/437; 562/453; 562/455; 562/456; 562/457; 562/458
[58] Field of Search .......... 260/518 R, 518 A, 501.15, 260/501.1, 519; 562/433, 437, 453, 456, 457, 458, 455

[56] References Cited

U.S. PATENT DOCUMENTS

| | | | |
|---|---|---|---|
| 3,639,249 | 2/1972 | Luethi et al. | 260/397.6 |
| 3,852,324 | 12/1974 | Wright | 260/465 D |
| 3,966,965 | 6/1976 | Sellsted et al. | 424/309 |
| 3,972,911 | 8/1976 | Wright et al. | 260/518 R |
| 3,987,192 | 10/1976 | Wright | 424/304 |

OTHER PUBLICATIONS

Rhone, Chemical Abstracts, vol. 60, 3012(e).

Primary Examiner—Bernard Helfin
Assistant Examiner—G. T. Breitenstein
Attorney, Agent, or Firm—Martin B. Barancik

[57] ABSTRACT

Compounds represented below

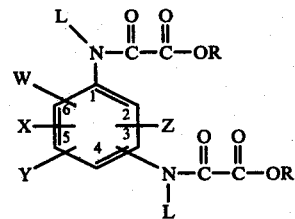

and pharmaceutical compositions thereof, the compositions including the non-substituted phenylene dioxamates are useful in the prophylactic treatment of sensitized mammals for allergy and all anaphylactic reactions of a reagin or non-reagin mediated nature.

35 Claims, No Drawings

DIOXAMIC ACIDS AND SALTS

CROSS REFERENCE TO RELATED APPLICATION

This application is a continuation of co-pending application Ser. No. 714,571, filed Aug. 16, 1976, abandoned, which is a division of application Ser. No. 382,762, filed July 26, 1973, issued as U.S. Pat. No. 3,993,679, which is a continuation-in-part application of Ser. No. 317,005, filed Dec. 20, 1972 now abandoned.

BRIEF SUMMARY OF THE INVENTION

It has now been discovered that novel compounds of FIG. 1 are useful in the prophylactic treatment of sensitized humans and animals for allergy and all anaphylactic reactions of a reagin or non-reagin mediated nature. The compounds are formulated with pharmaceutical carriers for oral, parenteral, inhalation or rectal means of administration.

DETAILED DESCRIPTION OF THE INVENTION

In accordance with this invention is provided compounds represented by FIG. 1 and hereafter referred to as Group A:

$$\text{I}$$

[Structure: substituted benzene ring with positions 1-6, bearing substituents W, X, Y, Z, and two —N(L)—C(O)—C(O)—OR groups]

wherein W, X, Y, and Z can be the same or different and are selected from the group consisting of hydrogen, alkyl from one to six carbon atoms, inclusive, phenyl, alkoxy with the alkyl group from one to six carbon atoms, inclusive, hydroxy, nitro, halogen, trifluoromethyl, cyano, with the proviso that cyano is meta to both $$\underset{\mathrm{L}}{-\mathrm{N}}-\underset{\mathrm{O}}{\overset{\mathrm{O}}{\mathrm{C}}}-\underset{\mathrm{O}}{\overset{\mathrm{O}}{\mathrm{C}}}-\mathrm{OR} \text{ groups, and } \mathrm{C}\overset{\nearrow\mathrm{O}}{\searrow\mathrm{Q}},$$

wherein Q is selected from $$\mathrm{OD}, \mathrm{N}\overset{R^1}{\underset{R^2}{\diagdown}}, \text{ and } \mathrm{NH}(\mathrm{CH}_2)_m\mathrm{N}\overset{R^1}{\underset{R^2}{\diagdown}},$$

wherein D is selected from the group consisting of hydrogen, alkyl from one to six carbon atoms, phenyl, $(CH_2)_m NR^1R^2$, and a pharmaceutically acceptable metal or amine cation with the proviso that where R is alkyl from one to six carbon atoms, inclusive, or phenyl, and Q is OD, then D is alkyl from one to six carbon atoms, inclusive, hydrogen, $$(CH_2)_m N\overset{R^1}{\underset{R^2}{\diagdown}} \text{ or phenyl,}$$

and when $$R \text{ is } (CH_2)_n N\overset{R^3}{\underset{R^4}{\diagdown}}$$

and Q is OD, then D is the same as R. When R is hydrogen or a pharmaceutically acceptable metal or amine cation, and Q is OD, then D is the same as $R_1$ m is 2 or 3; $R^1$ and $R^2$ are the same or different and are selected from the group consisting of hydrogen and alkyl from one to three carbon atoms, inclusive, and then taken together with the nitrogen atom to which they are attached, from an alicyclic ring of four to six carbon atoms; with the additional overall proviso that at least one of W,X,Y, and Z is not hydrogen when L is hydrogen.

L is selected from the group consisting of hydrogen, alkyl of from one to six carbon atoms, inclusive, benzyl, and monosubstituted benzyl wherein the substitutent is selected from the group consisting of alkyl from 1 to 4 carbon atoms, inclusive; and halogen.

The $$\underset{\mathrm{L}}{-\mathrm{N}}-\underset{\mathrm{O}}{\overset{\mathrm{O}}{\mathrm{C}}}-\underset{\mathrm{O}}{\overset{\mathrm{O}}{\mathrm{C}}}-\mathrm{OR} \text{ group}$$

is located at the 3 or 4 position and R is selected from the group consisting of hydrogen, alkyl from 1 to 6 carbon atoms, inclusive, phenyl, $$(CH_2)_n N\overset{R^3}{\underset{R^4}{\diagdown}}$$

and a pharmaceutically acceptable metal or amine cation, n is 2 or 3, $R^3$ and $R^4$ are the same or different and are selected from the group consisting of hydrogen, alkyl of from 1 to 3 carbon atoms, inclusive, and when taken together with the nitrogen atom to which they are attached, form an alicyclic ring of four to six carbon atoms.

Pharmaceutically acceptable salts of any of the above compounds are also within the invention.

Pharmaceutical compositions of Group A compounds are also in accordance with this invention, with the proviso that W, X, Y, and Z can all be hydrogen when L is hydrogen.

A further group of compounds are compounds wherein W is hydrogen and X, Y, Z, L, $$\underset{\mathrm{L}}{-\mathrm{N}}-\underset{\mathrm{O}}{\overset{\mathrm{O}}{\mathrm{C}}}-\underset{\mathrm{O}}{\overset{\mathrm{O}}{\mathrm{C}}}-\mathrm{OR},$$

and R are as previously defined in Group A.

A still further group of compounds are compounds wherein W and X are hydrogen, and Y, Z, L,

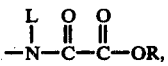

and R are as previously defined in Group A.

Another group of compounds are compounds wherein W, X, and Y are hydrogen, and Z, L,

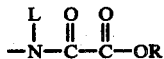

and R are as previously defined in Group A.

Another group of compounds, hereafter referred to as Group B, are compounds where W is hydrogen, X, Y, and Z are the sme or different and are selected from the group consisting of hydrogen, alkyl from one to three carbon atoms, inclusive, alkoxy with the alkyl group having from one to three carbon atoms, inclusive, hydroxy, nitro, halogen, trifluoromethyl, cyano, with the proviso that cyano is meta to both

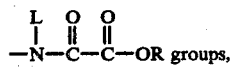
and

where Q is as previously defined in Group A with the proviso that when D is alkyl, the upper carbon atom limitation is three; with the proviso that at least one of X, Y, and Z is other than hydrogen when L is hydrogen; and the

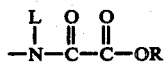

is as previously defined in Group A. R is selected from the group consisting of hydrogen, alkyl from one to three carbon atoms, inclusive, phenyl, and a pharmaceutically acceptable metal or amine cation, L is as previously defined in Group A.

Another group of compounds are where W and X are hydrogen, Y and Z are as previously defined in Group B, L,

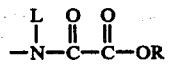

and R are as previously defined as in Group B.

A further group of compounds are where W, X and Y are hydrogen, Z, L,

and R as previously defined in Group B.

A still further group of compunds, hereafter referred to as Group C, are where W and X are hydrogen, Y and Z are the same or different and are selected from the group consisting of hydrogen, alkyl from one to three carbon atoms, inclusive, alkoxy with the alkyl group having from one to three carbon atoms, inclusive nitro, fluoro, chloro, trifluoromethyl, cyano, with the proviso that cyano is meta to both

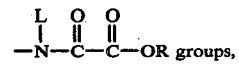

and

where Q is as defined in Group B, with the proviso that at least one of Y and Z is other than hydrogen when L is hydrogen.

L is selected from the group consisting of hydrogen and alkyl from one to three carbon atoms, inclusive;

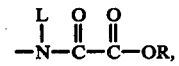

and R are as previously defined in Group B.

A further group of compounds are where W, X, and Y are hydrogen. Z is as defined in Group C. L,

and R are as defined in Group C.

A still further group of compounds hereinafter referred to as Group E of FIG. 1 are where W and X are hydrogen, Y and Z are the same or different and are selected from the group consisting of hydrogen, alkyl from one to three carbon atoms, inclusive, alkoxy with from one to three carbon atoms, inclusive, alkoxy with alkyl of one to three carbon atoms, inclusive, fluoro, chloro, trifluormethyl, cyano, with the proviso that cyano is meta to both

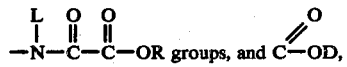

wherein D is selected from the group consisting of hydrogen, alkyl from one to three carbon atoms, inclusive, and a pharmaceutically acceptable metal or amine cation with the proviso that where R is alkyl from one to three carbon atoms, D is alkyl from one to three carbon atoms, inclusive, or hydrogen, and when R is hydrogen or a pharmaceutically acceptable metal or amine cation, D is the same as R, with the proviso that at least one of Y and and Z is other than hydrogen when L is hydrogen.

L is hydrogen,

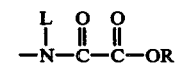

is at the 3 or 4 position and R is selected from the group consisting of hydrogen, alkyl from one to three carbon atoms, inclusive, and a pharmaceutically acceptable metal or amine cation.

A more preferred group of the Group E compounds are where Y and Z, as previously defined in Group E, are at the 2 and 5 position, L and R are as previously defined in Group E and

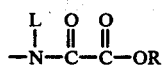

is at the 3 position.

A still more preferred group of the Group E compounds are where Y and Z, as previously defined in Group E, are at the 2 and 5 position, D is hydrogen or a pharmaceutically acceptable metal or amine cation with the proviso that where R is alkyl from one to three carbon atoms, D is hydrogen and where R is hydrogen or a pharmaceutically acceptable metal or amine cation, D is the same as R; L and R are as previously defined in Group E; and

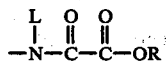

is at the 3 position.

Another group of preferred compounds are where W, X, and Y are hydrogen, Z is as previously defined in Group E and Z is at the 5 position and D is hydrogen or a pharmaceutically acceptable metal or amine cation with the proviso that where R is alkyl of from one to three carbon atoms, inclusive, D is hydrogen and when R is hydrogen or a pharmaceutically acceptable metal or amine cation, D is the same as R. L and R are as previously defined in Group E and

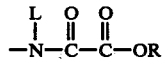

is at the 3 position.

The most preferred compound is N,N'-(5-cyano-m-phenylene)dioxamic acid.

As employed in the above disclosure and throughout the specification, the term "halogen" includes fluoro, chloro, bromo and iodo. The term "alkyl" includes methyl, ethyl, propyl, and isopropyl when limited to three carbon atoms, and additionally includes n-butyl, n-pentyl, n-hexyl and isomers thereof when limited to six carbon atoms. The term "pharmaceutically acceptable metal" includes alkali metals such as sodium and potassium, alkaline earth metals such as calcium and magnesium and other acceptble metals such as aluminum. The term "amine cation" includes all pharmaceutically acceptable cations from amine such as ammonia, tris(hydroxymethyl)-aminomethane, D-threo-2-amino-1-p-nitrophenyl-1,3-propanediol, N,N-bis(hydroxyethyl)piperazine, 2-amino-2-methyl-1-propanol, 2-amino-2-methyl-1,3-propanediol and 2,2-bis(hydroxymethyl)-2,2',2''-nitriolo-triethanol and further amines including $H_2NR'$, $HNR'_2$, and $NR'_3$, wherein R' is selected from the group consisting of alkyl from one to three carbon atoms, inclusive, and —$CH_2CH_2OH$.

The compounds of this invention can be prepared by methods known to the art. The appropriately substituted 3- or 4- amino anilines (II) are suitable starting materials. These compounds are reacted with an alkyl oxalyl halide, preferably ethyl oxalyl chloride (IIIa), in a suitable solvent and base to form the dioxamate (IV). An alternative method of preparing the dioxamate is to react (II) with a dialkyl oxalate, preferably diethyl oxalate (IIIb) in neat solution or with an additional solvent if necessary at a temperature ranging from about 25° C. to about reflux temperature of the system.

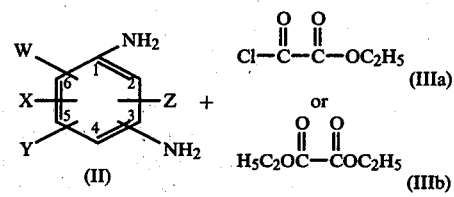

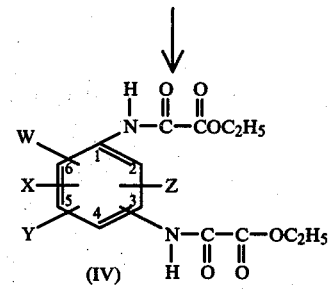

At this point of the synthetic pathway, the oxamate cam be transesterified to other esters and/or converted to the diacid by hydrolysis and thence to the metal or amine salts by standard methods.

In order to make compounds in accordance with the invention where L is other than hydrogen, the appropriately substituted 3- or 4- amino anilines are alkylated with the suitable alkylating agent under conventional alkylating conditions and then reacted with IIIa or IIIb. For example, compounds of Formula II are initially reacted with para-toluene sulfonyl chloride to form a sulfonamide. The sulfonamide is then alkylated with an L halide, preferably chloride, in the presence of base, for example, sodium hydroxide, to form the L substituted sulfonamide. The toluene sulfonyl grouping is then selectively hydrolyzed off with, for example, sulfuric acid and water, leaving an appropriately L substituted amino aniline compound of Formula II.

An alternative method of preparing compounds of Formula II where L is other than hydrogen is to acylate a Formula II compound by conventional means and then to reduce the acylated compound with $LiAlH_4$ or other suitable agents in a solvent such as ether or tetrahydrofuran to give the L substituted compound. For example, formylation followed by reduction would methylate the nitrogen. Benzoylation followed by reduction results in benzylating the nitrogen.

Examples of L substituents include methyl, ethyl, propyl, butyl, pentyl, hexyl, and isomers thereof; benzyl, 2-methylbenzyl, 3-propylbenzyl, 4-isohexylbenzyl, 4-chlorobenzyl, 3-bromobenzyl, 2-fluorobenzyl.

The appropriately W, X, Y, and Z substituted 3- or 4- amino anilines are prepared by conventional substitution methods. Depending upon the substituent itself, the placement of the substituent and the placement of the oxamic group, the substitution of the benzene ring can occur on the benzene itself, on itrobenzene, nitroaniline, dinitrobenzene, aminoaniline or combinations of these methods. Reduction of nitro to an amino grouping can be easily effected by catalytic means such as Raney Nickel, palladium on charcoal or platinum in the presence of hydrogen. Additionally, chemical means are also available for reduction of nitro to amino, for example, stannous chloride in concentrated hydrochloric acid and Iron in acetic acid with ethanol.

The particular substituents are prepared by converting the corresponding diamino or dinitro benzoic acid, for example, to the ester, amide, etc., by standard methods. This can be done prior to the preparation of the dioxamate from the substituted diamino starting material.

Once starting material II, or its L substituted analogue, is prepared, it is reacted with an alkyl oxalyl halide or dialkyl oxalate. When using an alkyl oxalyl halide, reaction is carried out in base and solvent at standard conditions. Examples of suitable solvents are dimethylformamide, dioxane, and tetrahydrofuran. Appropriate bases include triethylamide, N-methylmorpholine, dimethylpiperazine, and N-methylpiperidine. When the dialkyl oxalate is employed, the starting material II or its substituted analogue is heated together with the dialkyl oxalate or an additional solvent such as a xylene or diphenyl ether if desired, thereby forming the dioxamate. The temperature is from about 25° C. to the reflux temperature of the system.

The dioxamate is then readily converted to the dioxamic acid by using dilute base such as sodium hydroxide, potassium hydroxide or potassium carbonate at temperatures ranging from about 25° to 100° C., followed by addition of acid. The alkaline metal salts of the oxamate may be soluble in aqueous medium or relatively insoluble. If soluble in aqueous medium, the pH is adjusted with acid and the resulting precipitate is collected. If the alkaline metal salt is insoluble in aqueous medium, the precipitate per se can be collected and then heated in aqueous acid to an appropriate temperature, collecting the mixture and isolating the desired diacid. The acid can then be easily converted to the metal or amine salt by contacting the diacid with two equivalents of the desired amine or metal and heating in a sufficient amount of water to effect solubilization. The crystalline salts can be precipitated by the addition of an organic solvent, for example, methanol.

Following is an illustrative list of compounds of the invention which can be prepared by the above disclosed procedures:

TABLE I

A.

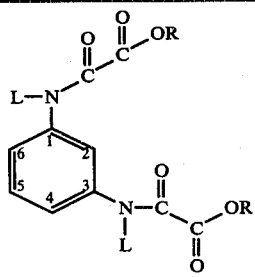

L and R are hydrogen

Position and Substituent
5-F
5-Cl
5-Br
5-I
5-CH$_3$
5-C$_2$H$_5$
5-C$_3$H$_7$
5-iC$_3$H$_7$
5-NO$_2$

TABLE I-continued
5-OCH$_3$
5-OC$_2$H$_5$
5-OC$_3$H$_7$
5-OiC$_3$H$_7$
5-C$_4$H$_9$
5-C$_5$H$_{11}$
5-OC$_4$H$_9$
5-OC$_5$H$_{11}$
5-OC$_6$H$_{13}$
5-OiC$_5$H$_{11}$
5-OiC$_6$H$_{13}$
5-C$_6$H$_{13}$
5-iC$_4$H$_9$
5-IC$_5$H$_{11}$
5-iC$_6$H$_{13}$
5-tBu
5-CF$_3$
5-COOH

5-CONHCH$_2$CH$_2$N(CH$_3$)$_2$

5-CONHCH$_2$CH$_2$N(CH$_2$-CH$_2$)$_2$

5-CONH(CH$_2$)$_3$N(CH$_2$CH$_3$)$_2$

5-OH
5-CONH$_2$
5-CON(CH$_3$)(C$_2$H$_5$)

The unsubstituted dioxamic acid is monosubstituted at the 2 or 4 position with each of the above substituents.

5-CN
4,6-diCl
4,6-diCl; 2-NO$_2$
4,6-diiC$_3$H$_7$
4,6-diCH$_3$, 5-NO$_2$
4,6-diNO$_2$
2-OCH$_3$, 5-NO$_2$
5-Br, 4-C$_2$H$_5$
4-tC$_4$H$_9$, 5-iC$_3$H$_7$
4-tC$_4$H$_9$, 6-iC$_3$H$_7$
4-tC$_4$H$_9$, 6-NO$_2$
4,6-diCF$_3$
4-Cl, 6-NO$_2$
2,5-di-tC$_4$H$_9$
2,4-diCl
2,5-diOCH$_3$
2,4-diCH$_3$
2,4-diCF$_3$
2,4-diC$_2$H$_5$
2,4-diNO$_2$
4-Cl, 6F
4-Cl, 6-NO$_2$
4,6-diC$_2$H$_5$
4-CF$_3$, 5-CN
4,5-diC$_2$H$_5$
4,6-diF
4,5-diOCH$_3$
2,5-diCH$_3$
4,6-diOCH$_3$
4-Cl, 5-COOH
4,5-diCH$_3$
4,6-diCH$_3$
4,6-ditC$_4$H$_9$
4,6-diiC$_3$H$_7$
2-Cl, 5-CH$_3$
4-NO$_2$, 6-CF$_3$
2-Cl, 5-C$_2$H$_5$
2-Cl, 5-C$_3$H$_7$
2-Cl, 5-C$_4$H$_9$
2-Cl, 5-tC$_4$H$_9$
2-F, 5-C$_2$H$_3$
2-OC$_3$H$_7$, 5-CN
2-Br, 5-C$_3$H$_7$
2-Cl, 5-CF$_3$
2-Cl, 5-CN

TABLE I-continued

4-Cl, 5-CN
2-OH, 4-CF$_3$
2-CH$_3$, 5-CN
2-C$_3$H$_7$, 5-CN
2-F, 5-CN
2-CH$_3$, 5-COOH
2-NO$_2$, 5-COOH
2-Cl, 5-CH$_3$
2-Cl, 5-COOH
2-OH, 5-COOH
2-C$_4$H$_9$, 5-CN
2-Cl, 4-CH$_3$
2-CH$_3$, 4-OCH$_3$
2-NO$_2$, 4-Cl
4-COOH, 5-CN
4-NO$_2$, 5-CN
4-CH$_3$, 5-CN
4-OC$_2$H$_5$, 5-CN
4-OC$_2$H$_5$, 5-Cl
4-NO$_2$, 5-C$_2$H$_5$
4-CH$_3$, 5-OC$_2$H$_5$
4-F, 5-C$_3$H$_7$
4-OC$_2$H$_5$, 6-C$_2$H$_5$
4-CH$_3$, 6-Cl
4-F, 6-OCH$_3$
2-CONH$_2$, 5-CN
2-Cl, 5-CONH$_2$
2-CH$_3$, 5-CONH$_2$
2-OC$_2$H$_5$, 5-CONH$_2$
2-CONH$_2$, 5-C$_2$H$_5$
2-CONH(CH$_2$)$_3$N(CH$_3$)$_2$
4-Cl, 6-CONH(CH$_2$)$_2$NH$_2$
4-Cl, 5-COOH
4-Cl, 5-CN
2-CF$_3$, 5-COOH
2-iC$_5$H$_7$, 5-COOH
2-OC$_2$H$_5$, 5-COOH
2-OCH$_3$, 5-CN
2-NO$_2$, 5-CN
2-COOH, 5-CN
2-OH, 5-CN
2-CF$_3$, 5-CN
2,4,6-tri-iC$_3$H$_7$
2,4-6-tri-CH$_3$
4Br; 2-6-di-NO$_2$
4-Cl, 2-6-di-NO$_2$
2,4,6-tri-Cl
5-CN, 4,6-di-CH$_3$
5-COOH, 4,6-di-CH$_3$
4,6-di-CH$_3$, 5-NO$_2$
2-C$_2$H$_5$; 4,6-di-CH$_3$
4-OCH$_3$; 2,6-di-NO$_2$
2,4,6-tri-C$_2$H$_5$
2,4,5-tri-F
5-CN, 4-6-di-COOH
4,5,6-tri-CH$_3$
2,4-di-F; 5-NO$_2$
4,6-di-OCH$_3$; 5-NO$_2$
4-C$_2$H$_5$; 2,6-di-iC$_3$H$_7$
2,4,5-tri-OCH$_3$
2,4,6-tri-NO$_2$
2,4,5,6-tetra-CH$_3$
2,4,5,6-tetra-Cl
2,4,5,6-tetra-OC$_2$H$_5$
2,4,6-tri-CH$_3$; 5-CN
2,4,6-tri-CH$_3$; 5-COOH

TABLE I-continued

B.

[Structure: benzene ring with positions labeled 1-6, where position 1 bears N(L)-C(=O)-C(=O)-OR and position 4 bears N(L)-C(=O)-C(=O)-OR]

L and R are hydrogen.

| Substituent and Position |
|---|
| 2-CH$_3$ |
| 2-C$_2$H$_5$ |
| 2-C$_3$H$_7$ |
| 2-C$_4$H$_9$ |
| 2-iC$_4$H$_9$ |
| 2-tC$_4$H$_9$ |
| 2-C$_5$H$_{11}$ |
| 2-C$_6$H$_{13}$ |
| 2-F |
| 2-Cl |
| 2-Br |
| 2-I |
| 2-OCH$_3$ |
| 2-OC$_2$H$_5$ |
| 2-NO$_2$ |
| 2-CF$_3$ |
| 2-COOH |
| 2-OC$_3$H$_7$ |
| 2-OC$_4$H$_9$ |
| 2-OiC$_5$H$_{11}$ |
| 2-OC$_6$H$_{13}$ |
| 2-OH |
| 2-CONH$_2$ |
| 2-CON(C$_2$H$_5$)$_2$ |
| 2-CONH(CH$_2$)$_2$N(CH$_3$)$_2$ |
| 2-CONH(CH$_2$)$_3$N(CH$_2$CH$_2$)$_2$CH$_2$CH$_2$ |
| 2,5-diCl |
| 2,3-diCl |
| 2,6-diCl |
| 2,3-diCH$_3$ |
| 2,5-diCH$_3$ |
| 2,6-diCH$_3$ |
| 2,5-diF |
| 2,6-diBr |
| 2,6-diNO$_2$ |
| 2-Cl, 5-OCH$_3$ |
| 2-Cl, 5-NO$_2$ |
| 2,5-diOC$_2$H$_5$ |
| 2,3-diOC$_2$H$_5$ |
| 2,6-diOC$_2$H$_5$ |
| 2,6-diC$_2$H$_5$ |
| 2,5-diOCH$_3$ |
| 2-OCH$_3$, 5-NO$_2$ |
| 2-Cl, 6-OCH$_3$ |
| 2,5-di tC$_4$H$_9$ |
| 2,3-diEt |
| 2-Cl, 3-OCH$_3$ |
| 2-Cl, 5-CH$_3$ |
| 2,6-di tC$_4$H$_9$ |
| 2,6-diF |
| 2,3-diCOOH |
| 2,5-diCONH$_2$ |
| 2,6-diCONH(CH$_2$)N(CH$_2$CH$_3$)$_2$ |
| 2-F, 6-iC$_3$H$_7$ |
| 2-CH$_3$, 5-OC$_3$H$_7$ |

TABLE I-continued

2-CF₃, 5-C₂H₅
2,3-diNO₂
2,5-diNO₂
2-Cl, 3-C₂H₅
2-F, 3-NO₂
2-Br, 3-CF₃
2-Cl, 5-COOH
2-F, 6-CONH₂
2-CH₃, 3-OiC₃H₇
2-C₂H₅, 3-CH₃
2-C₃H₇, 5-CH₃
2-CH₃, 6-C₂H₅
2-OH, 5-OC₂H₅
2-OC₂H₅, 5-OH
2-CH₃, 5-COOH
2-OCH₃, 6-COOH
2-OC₂H₅, 5-OC₄H₉
2-OCH₃, 6-OC₂H₅
2-OH, 6-CONH₂
2-CF₃, 6-OC₂H₅
2-OH, 6-C₂H₇
2,3,5-tri-Cl
2,3,5-tri-CH₃
2,3,5-tri-OC₂H₅
2,3,5-tri-OH
2,3,5-tri-COOH
2-C₂H₅; 3,5,6-tri-CH₃
2,3,5,6-tetra-CH₃
2,3,5-tri-Cl; 6-OCH₃
2,3,5,6-tetra-Cl
2-C₄H₉; 3,5,6-tri-CH₃
2,3,5,6-tetra-F
2,3,5,6-tetra-C₂H₅
2,3,5-tri-CH₃; 6-C₃H₇
2,3,5,6-tetra-OC₂H₅

TABLE II

A.

L—N(—C(=O)—C(=O)—OR) attached to phenyl ring positions 1 and 3, with second N—C(=O)—C(=O)—OR group, L substituent on N.

L is hydrogen and R is alkyl from one to six carbon atoms, or phenyl, preferably C₂H₅.

Position and Substituent

5-COOH
5-CONH₂
5-CON(CH₃)(C₂H₅)
5-COOCH₃
5-COOC₂H₅
5-COOC₃H₇
5-COOC₄H₉
5-COOiC₄H₉
5-COOiC₅H₁₁
5-COOC₆H₁₃
5-CONH(CH₂)₃N(CH₂CH₂)₂CH₂ (morpholine-like)
5-COOC₆H₅
5-CO₂(CH₂)₂N(CH₃)₂

The unsubstituted dioxamic acid is monosubstituted at the 2 or 4 position with each of the above substituents.

2-5-diCOOH
2,5-diCON(CH₃)(C₂H₅)
2,5-diCOOC₃H₇
2,5-di-COOC₅H₁₁
2,5-diCONH(CH₂)₂N(CH₃)₂
4,6-diCOOH
4,6-diCOOiC₄H₉

TABLE II-continued 4,5-diCOOCH₃
2,4-diCONH₂
2-COOH, 5-CN
4-COOH, 5-CN
2-COOC₂H₅, 5-CN
2-C₂H₅, 5-COOH
2-Cl, 5-COOH
2-OCH₃, 5-COOH
2-Cl, 5-CN
2-NO₂, 5-COOH
2-CF₃, 5-COOH
4-CH₃, 5-COOCH₃
4-OC₂H₅, 5-COOiC₄H₉
4-F, 5-CONH₂
4-CF₃, 5-CONH(CH₂)₂N(CH₃)₂
4,6-diCH₃, 5-COOH
4,6-diC₂H₅, 2-COOCH₃
2,4,6-tri-CH₃, 5-COOH
4,5,6-tri-COOH
4-OH, 5-COOH
2-NO₂, 5-COOH, 6-Cl
4,5,6-tri-C₂H₅, 2-COOH

B.

L—N(—C(=O)—C(=O)—OR) on phenyl ring position 1, with second N—C(=O)—C(=O)—OR group at position 4, L substituent.

L is hydrogen, R is alkyl from 1 to 6 carbons or phenyl, preferably C₂H₅.

Position and Substituent

2-COOH
2-CONH₂
2-CON(CH₃)(C₂H₅)
2-COOCH₃
2-COOC₂H₅
2-COOC₃H₇
2-COOC₄H₉
2-COOiC₄H₉
2-COOiC₅H₁₁
2-COOC₆H₁₃
2-CONH(CH₂)₃N(CH₂—CH₂)(CH₂—CH₂) (pyrrolidine-like)
2-COOC₆H₅
2-CO(CH₂)₂NH₂
2,6-diCOOH
2,6-diCON(CH₃)(C₂H₅)
2,6-diCOOC₃H₇
2,6-diCOOC₅H₁₁
2,6-diCONH(CH₂)₂N(CH₃)₂
2,5-diCOOH
2,5-diCOOiC₄H₉
2,3-diCOOCH₃
2,3-diCONH₂
2,5-diCONH(CH₂)₂NH₂
2-COOH, 3-C₂H₅
2-CONH₂, 3-OCH₃
2-COOC₂H₅, 3-Cl
2-COOC₃H₇, 3-NO₂
2-COOH, 5-C₂H₅
2-CONH₂, 5-OC₂H₅
2-COOC₂H₅, 5-F
2-COOC₃H₇, 5-CF₃
2-COOH, 6-C₃H₇
2-CONH₂, 6-OCH₃
2-COOCH₃, 6-Cl
2-COOC₃H₇, 6-NO₂
2,6-diCOOH, 3,5-diCH₃
2-COOH; 3,5,6-triC₂H₅

TABLE II-continued 2,6-diCOOCH$_3$, 3,5-diOC$_2$H$_5$
2-diCONH$_2$, 3,5,6-triCl
2-COOH; 3,5,6-triOCH$_3$

TABLE III

The compounds of Table I are converted to pharmaceutically acceptable salts, particularly tris(hydroxymethyl)methylammonium by standard methods.

Table III is not rendered in the same manner as Table I for the purpose of brevity. However, the same scoping is intended.

TABLE IV

The compounds of Table I are prepared where L is selected from the group consisting of alkyl from one to six carbon atoms, inclusive; benzyl and monosubstituted benzyl wherein the substituent is selected from the group consisting of alkyl of from one to four carbon atoms, inclusive, and halogen. Preferred compounds are where L is alkyl of from one to three carbon atoms, inclusive.

TABLE V

The compounds of Table IV are converted to pharmaceutically acceptable salts, particularly tris(hydroxymethyl)methylammonium, by standard methods.

TABLE VI

The compounds of Table II are prepared wherein L is selected from the group consisting of alkyl from one to six carbon atoms, inclusive; benzyl and monosubstituted benzyl wherein the substituent is selected from the group consisting of alkyl of from one to four carbon atoms, inclusive, and halogen. Preferred compounds are where L is alkyl of from one to three carbon atoms, inclusive.

TABLE VII

The compounds of Table I and Table IV are prepared wherein R is selected from the group consisting of alkyl from one to six carbon atoms, and phenyl.

The following examples are compounds in accordance with this invention. The compounds are intended not to limit but merely to exemplify the invention.

EXAMPLE 1

N,N'-(p-Phenylene)dioxamic acid a. Diethyl N,N'-(p-phenylene)dioxamate

A mixture of p-phenylenediamine (10.8 grams, 0.10 ml.) and diethyl oxalate (50 grams) is heated at reflux for three hours. The cooled reaction mixture is diluted with ether (200 ml.) and the solid product collected by filtration (21.4 grams, H.P. 215°–218° C.).

Analysis Calcd. for: C$_{14}$H$_{16}$N$_2$O$_6$: c, 54.54; H, 5.23; N, 9.09. Found: C, 54.58; H, 5.28; N, 9.11. uv (EtOH) λ max (ε): 208 sh (10,550), 216 sh (8,450), 306 (17,200). ir (Nujol): NH 3240; C=O 1735, 1685; Amide II/C=C 1565, 1515; C—O/C—N 1280, 1185, 1025.

b. Product

Diethyl N,N'-(p-phenylene)dioxamate (9.0 grams) is heated at reflux for two hours in 1.0N aqueous sodium hydroxide (200 ml.). The insoluble disodium salt is collected by filtration and then heated at 80°–90° in 1.0N HCl (100 ml.) for 0.5 hour. The desired diacid is collected by filtration (5.26 grams, M.P. >320°).

An analytical sample of the disodium salt is prepared by recrystallization from water.

Analysis Calcd. for: C$_{10}$H$_6$O$_6$N$_2$Na$_2$: C, 40.55; H, 2.04; N, 9.46; Na, 15.53. Found: C, 40.35; H, 2.14; N, 9.50; Na, 15.22. uv (H$_2$O) λ max (ε): 284 (14,800). ir (Nujol): NH 3320; C=O/CO$_2$/C=C 1695, 1675, 1650; Amide II C=C/CO$_2$ 1550, 1515.

EXAMPLE 2

N,N'-(m-phenylene)dioxamic acid a. Diethyl N,N'-(m-phenylene)dioxamate

A mixture of m-phenylenediamine (10.8 grams) 0.10 ml.) and diethyl oxalate (50 ml.) is refluxed for 2.5 hours. The cooled reaction mixture is diluted with ether (200 ml.) and the crude product collected (19.2 grams, M.P. 150° C.). Two recrystallizations from methanol give off white crystals (6.65 grams, 155°–160°).

b. Product

Diethyl N,N'-(m-phenylene)dioxamate (1.0 gram) is stirred in 1.0N aqueous sodium hydroxide for 0.5 hour. The solution is diluted with water (100 ml.) and the pH adjusted to pH 3 with concentrated hydrochloric acid. The resulting precipitate is collected and recrystallized from ethanol (0.46 grams, M. P. 240° C.).

Analysis Calcd. for C$_{10}$H$_6$N$_2$O$_6$: C, 47.62; H, 3.20; N, 11.11. Found: C, 47.21; H, 4.17; N, 9.77.

Analysis Calcd. for: C$_{10}$H$_8$N$_2$O$_8$·C$_2$H$_5$CH: C, 48.32; H, 4.70; N, 9.40. Found: C, 48.05; H, 4.57; N, 9.73. ir (Nujol): NH/OH 3520, 3430, 3340, 3310, 3160; acid OH 2650, 2500, 1925 (broad); C=O 1695, 1685; C=C/amide II 1615, 1550, 1485.

EXAMPLE 3

N,N'-Carboxy-m-phenylene)dioxamic acid a. Diethyl, N,N'-(5-carboxyphenylene)dioxamate A mixture of 3,5-diaminobenzoic acid (15.2 grams, 0.1 ml.) and diethyl oxalate (50 ml.) is heated at reflux for two hours. The cooled reaction mixture is diluted with ether and the crude product collected by filtration. Recrystallization from methanol gives a white solid (15.6 grams, M.P. 231° C.).

Analysis Calcd. for: C$_{15}$H$_{16}$O$_8$N$_2$: C, 51.15; H, 4.58; N, 7.95. Found: C, 50.65; H, 4.45; N, 8.06. ir (Nujol): NH 3220, 3160; NH/=CH3070; acid OH 2630, 2560; C=O 1740 1705 sh, 1690; C=C/amide II, 1610, 1555. uv (EtOH) λ max (ε):246 (17,300), 262 (16,500) 315 sh (4,900).

b. Product

Diethyl N,N'-(5-carboxy-m-phenylene)dioxamate (1.0 gram) is stirred in 1.0N aqueous sodium hydroxide (50 ml.) for 0.5 hour. The reaction mixture is diluted with water (100 ml.) and the pH adjusted to 3 with concentrated hydrochloric acid. The resulting precipitate is collected by filtration (0.80 gram, M.P.>320°).

EXAMPLE 4

N,N'-(2-Chloro-m-phenylene)dioxamic acid a. Diethyl N,N'-(2-chloro-m-phenylene)dioxamate A mixture of 2-chlorophenylene-1,3-diamine (2.0 grams) and diethyl oxalate (20 ml.) is refluxed for twelve hours. The cooled reaction mixture is diluted with Skellysolve B® and the crude solid collected. Recrystallization and treatment with Darco® give a white solid (2.05 grams, M.P. 162°).

Analysis Calcd. for: $C_{14}H_{15}N_2O_6Cl$: C, 49.06; H, 4.41; N, 8.18; Cl, 10.35. Found: C, 47.97; H, 4.12; N, 8.89; Cl, 10.63. uv (EtOH) λ max (ε): 215 sh (12,200), 228 sh (10,500), 263 (15,000). ir (Nujol): NH/OH 3380, 3360;=CH 3120; C=O 1720; C=C/amide II 1605, 1560, 1525; aromatic CH 795.

b. Product

Diethyl N,N'-(2-chloro-m-phenylene)dioxamate (0.50 gram) is heated at reflux in 1.0N aqueous sodium hydroxide (10 ml.) for one hour. The reaction mixture is diluted with water (15 ml.). Concentrated hydrochloric acid is added to pH 3 and the solid product collected by filtration (0.27 grams, M.P.>320°).

EXAMPLE 5

N,N'-(5-Cyano-m-phenylene)dioxamic acid a. 3,5-Diaminobenzonitrile

To a solution of 210 grams of stannous chloride dihydrate in 590 ml. of concentrated hydrochloric acid is added portionwise 25 grams of 3,5-dinitrobenzonitrile. The mixture is stirred for three hours at room temperature, then cooled to 0° in an ice-salt bath and a cold 50% sodium hydroxide solution added to the mixture until the mixture is strongly basic. During the addition the temperature is kept below 5°.

The mixture is extracted with methylene chloride and the solvent removed. There is obtained 2.25 grams of material melting at 185°-8°. Recrystallization from ethanol raises the melting point to 188°-9°.

Analysis Calcd. for: $C_7H_7N_3$: C, 63.14; H, 5.30; N, 31.56. Found: C, 62.87; H, 5.19; N, 31.72.

b. Diethyl N,N'-(5-Cyano-m-phenylene)dioxamate

A solution of 2.00 grams (0.015 mole) of 3,5-diaminobenzonitrile in 34 ml. of dry dimethylformamide and 3.5 grams of triethylamine is cooled to 0°. 4.09 grams (0.03 mole) of ethyl oxalyl chloride is added slowly to this solution. The reaction mixture is stirred in the ice-bath for two hours and then allowed to warm to room temperature overnight. The precipitate is removed by filtration and the filtrate poured into 200 ml. of water. The precipitate is removed by filtration and recrystallized from ethanol. There is obtained 1.91 gram of cream platelets melting at 189°-90°.

Analysis Calcd. for: $C_{15}H_{15}N_3O_6$: C, 54.05; H, 4.54; N, 12.61. Found: C, 53.89; H, 4.52; N, 12.92.

c. Product

A solution of 1.51 gram (0.0045 mole) of diethyl N,N'-(5-cyano-m-phenylene)dioxamate in 10 ml. of 5% sodium hydroxide solution is stirred for 25 minutes and filtered. To the filtrate is added dilute hydrochloric acid. The resulting precipitate is removed by filtration; weight 0.86 grams. M.P. 230° C.

Analysis Calc'd. for: $C_{11}H_7N_3O_6.H_2O$: C, 44.75; H, 3.07; N, 14.24. Found: C, 45.23; H, 3.22; N, 14.78.

EXAMPLE 6

N,N'-(2-Chloro-5-cyano-τ-phenylene(dioxamic acid a. 4-Chloro-3,5-diaminobenzonitrile

To a solution of 352.5 grams (1.56 mole) of stannous chloride dihydrate in 860 ml. of concentrated hydrochloric acid is added 50 gm. (0.2195mole of 4-chloro-3,5-dinitrobenzonitrile. The mixture is stirred at room temperature for two hours and cooled to 0° in an ice-salt bath. A cold solution of 50% sodium hydroxide is added to the mixture until strongly basic. During the addition the temperature is kept below 30°.

The precipitate is removed by filtration and extracted three times with 400 ml. of ethyl acetate. The extracts are combined and added to the aqueous filtrate. The phases are shaken well for ten minutes and separated. The organic phase is evaporated to dryness in vacuo. The solid residue is recrystallized from ethanol-water. There is obtained 25.0 grams (68%) of tan needles melting at 169°-170°.

Analysis Calc'd. for: $C_7H_6ClN_3$: C, 50.16; H, 3.61; Cl, 21.16; N, 25.07. Found: C, 49.91; H, 3.61; Cl, 21.30; N, 24.86.

b. Diethyl N,N'-(2-Chloro-5-cyano-m-phenylene)dioxamate

To a solution of 56.2 gm. (0.34 mole) of 4-chloro-3,5-diaminobenzonitrile in 160 ml. of dry dimethylformamide is added 82.8 gm. (0.82 mole) of triethylamine. The solution is cooled to 5° in an ice bath and there is added 112 gm. (0.82 mole) of ethyloxalyl chloride dropwise, keeping the temperature less than 15°. The mixture is stirred in an ice bath for one hour and warmed to room temperature. The mixture is stirred at room temperature for 24 hours. The precipitate is removed by filtration and washed two times with ethyl acetate. The filtrate and washes are combined and the ethyl acetate distilled off in vacuo. The dimethylformamide solution is poured into three liters of water. The semi-solid residue is removed by filtration. The residue is recrystallized from ethanol. There is obtained 72.4 gm. (58%) of yellow needles melting at 177°-179°.

Analysis Calc'd. for: $C_{15}H_{14}ClN_3O_6$: C, 48.99, H, 3.84; Cl, 9.64; N, 11.43. Found: C, 48.94; H, 3.84; Cl, 9.80; N, 11.20.

c. Product

A solution of 72.4 gm. (0.197 mole) of diethyl N,N'-(2-chloro-5-cyano-m-phenylene)dioxamate in 750 ml. of methylene chloride is extracted with 465 ml. of 1N sodium hydroxide. The aqueous phase is separated and stirred for 20 minutes at room temperature. The solution is acidified with dilute hydrochloric acid. The precipitate is removed by filtration and washed with water. There is obtained 59.1 gm. (96%) of material melting at 212° (dec.).

Analysis Calc'd. for: $C_{11}H_6N_9ClO_8$: C, 42.39, H, 1.94; N, 13.48; Cl, 11.38. Found: C, 42.08, H, 1.82; N, 13.40; Cl, 11.60. Infrared: (Nujol) 3480, 3560 (NH) 2630, 2500 (acid OH), 2240 (C≡N) 1710 (C=O), 1590, 1515 (C=C/amide 11) cm$^{-1}$Ultraviolet: λ max (0.1N NaOH) 239.5 (23,800) sl.sh. 300 (3,250) m.u.

EXAMPLE 7

(5-Carbamoyl-m-phenylene)dioxamic acid hydrate a. 3,5-Diaminobenzamide

A solution of 20.5 gm. (0.097 mole) of 3,5-dinitrobenzamide in 450 ml. of an ethyl acetate-ethanol mixture (2:1) is hydrogenated at 3 atmospheres of hydrogen using 1 gm. of 10% palladium on charcoal as catalyst. When absorption of hydrogen is complete, the catalyst is removed by filtration and the filtrate is concentrated to dryness under reduced pressure and the residue recrystallized from water. There is obtained 11.65 gm. (79% of long yellow needles melting at 108°-9°.

b. Diethyl (5carbamoyl-m-phenylene)dioxamate

To a stirred solution of 7.56 gm. (0.05 mole) of 3,5-diaminobenzamide and 12.12 gm. (0.12 mole) of triethylamine in a mixture of 15 ml. of dry dimethylformamide and 75 ml. of dry ethyl acetate, cooled to 0° in an ice-bath, is added dropwise, under a nitrogen atmosphere, 16.4 gm. (0.12 mole) of ethyloxalyl chloride. During the addition the temperature is kept below 15°. The mixture is stirred in the ice-bath for two hours and allowed to stand at room temperature overnight.

The precipitate is removed by filtration and washed with dry ethyl acetate. The precipitate is stirred with 400 ml. of water for 30 minutes and the undissolved material removed by filtration and recrystallized from aqueous ethanol. There is obtained 10.05 gm. (57%) of yellow-tinted needles melting at 213°-5°.

Analysis Calc'd. for: $C_{15}H_{17}N_3O_7$: C, 51.30; H, 4.88; N, 11.96. Found: C, 51.53; H, 4.95; N, 12.13.

c. Product

A mixture of 5.26 gm. (0.015 mole) of diethyl (5-carbamoyl-m-phenylene)dioxamate, 33 ml. of 1N sodium hydroxide solution and 50 ml. of water is stirred for twenty minutes. Methylene chloride (85 ml.) is added and stirring continued for an additional thirty minutes. The aqueous layer is separated and acidified by the addition of dilute hydrochloric acid. The precipitate is removed by filtration and washed with water. The solid is purified by dissolving it in a dilute solution of THAM, filtering the solution and reprecipitation by the addition of a filtered solution of dilute hydrochloric acid. There is obtained 4.7 gm. of material melting at 220° (dec.).

The infrared spectra is in agreement.

EXAMPLE 8

N,N'-(4-Chloro-5-cyano-m-phenylene)dioxamic acid a. 2-Chloro-3,5-dinitrobenzoyl chloride

A mixture containing 50.5 gm. (0.205 mole) 2-chloro-3,5-dinitrobenzoic acid and 42.69 gm. (0.205 mole) of phosphorous pentachloride is heated at reflux for 1.5 hours. The phosphorous oxychloride formed is removed by distillation under vacuum and the residue recrystallized from benzene-cyclohexane. There is obtained 37.0 gm. (68%) of long colorless needles melting at 59°-60°.

b. 2-Chloro-3,5-dinitrobenzamide

A mixture of 37.0 gm. (0.14 mole) of 2-chloro-3,5-dinitrobenzoyl chloride and 100 ml. of concentrated ammonium hydroxide is placed in a mortar, ground for ten minutes and allowed to stand for one hour. The yellow precipitate is removed by filtration and washed with water. There is obtained 32.3 gm. (94%) of material melting at 181°-3°.

c. 2-Chloro-3,5-dinitrobenzonitrile

A mixture of 31.8 gm. (0.129 mole) of 2-chloro-3,5-dinitrobenzamide and 50 ml. of phosphorous oxychloride is heated under reflux for one hour. The excess phosphorous oxychloride is removed by distillation under reduced pressure. To the residue is cautiously added ice water. The light yellow-green solid is removed by filtration and washed with water. There is obtained 28.0 g. (95%) of material melting at 139°-41°.

d. 2-Chloro-3,5-diaminobenzonitrile

To a solution of 19- gm. (0.86 mole) of stannous chloride dihydrate in 475 ml. of concentrated hydrochloric acid is added 27.5 gm. (0.12 mole) of 2-chloro-3,5-dinitrobenzonitrile. The temperature rises to 84° and a solution occurs. The mixture is allowed to cool to room temperature, placed in an ice-bath, cooled to 0° and a cold 50% sodium hydroxide solution is added, with cooling, until the mixture is strongly basic. The gelatinous precipitate is removed by filtration. The precipitate is washed thoroughly (4 times) with portions of ethyl acetate. The combined ethyl acetate washes are used to extract the aqueous filtrate. The combined ethyl acetate extracts are dried over anhydrous MgSO4 and the solvent removed by distillation. The residue is recrystallized for ethanol. There is obtained 11.30 gm. (56%) of colorless needles melting at 181°-82°.

Analysis Calc'd. for: $C_7H_6ClN_3$: C, 50.16; H, 3.61; Cl, 21.16%. Found: C, 50.45; H, 3.80; Cl, 20.77%.

e. Diethyl N,N'-(4-chloro-5-cyano-m-phenylene)dioxamate

To a stirred solution of 10.18 gm. (0.06 mole) of 2-chloro-3,5-diaminobenzonitrile in 30 ml. of dry dimethylformamide, 14.57 gm. (0.144 mole) of triethylamine and 100 ml. of dry ethyl acetate, cooled to 5° in an ice-bath, are added, dropwise, 19.66 gm. (0.144 mole) of ethyloxalyl chloride. The mixture is stirred in the ice-bath for one hour and then allowed to stand overnight at room temperature.

The precipitate is removed by filtration and washed with dry ethyl acetate. The filtrate and washings are combined and most of the solvent is removed by distillation under reduced pressure. The residue is poured into 800 ml. of water and stirred for one hour. The water is decanted off and the residue recrystallized from absolute ethanol. There is obtained 16.60 gm. (75%) of a yellow solid melting at 154°-6°. An additional recrystallization gives yellow needles melting at 153°-154°.

Analysis Calc'd. for: $C_{15}H_{14}ClN_3O_6$: C, 48.99; H, 3.84; Cl, 9.64; N, 11.43%. Found: C, 49.15; H, 4.04; Cl, 9.73; N, 11.26%.

f. Product

To 100 ml. of methylene chloride in a separating funnel is added 5.52 gm. (0.015 mole) of diethyl N,N'-(4-chloro-5-cyano-m-phenylene)dioxamate, 36 ml. of a 1N sodium hydroxide solution and 100 ml. of water. The mixture is shaken for ten minutes. The aqueous layer is separated, stirred for an additional ten minutes and acidified with dilute hydrochloric acid. The yellow precipitate is removed by filtration and washed with water. There is obtained 4.62 gm. (99%) of material melting above 300°. A sample is recrystallized from water for analysis.

Analysis Calc'd. for: $C_{11}H_6N_3ClO_6 \cdot H_2O$: C, 40.08; H, 2.44; Cl, 10.76; N, 12.75. Found: C, 40.57; H, 1.90; Cl, 11.36; N, 13.25. The infrared and NMR spectra are in agreement. uv λ max (0.1N NaOH) 242 (21,200) 318 (3,650) m.u.

EXAMPLE 9

N,N'-[2-Chloro-5-(trifluoromethyl)-m-phenylene]dioxamic acid a. 4-Chloro-3,5-diamine-α,α,α-trifluorotoluene

To a stirred solution of 90.24 gm. (0.4 mole) of stannous chloride dihydrate in 220 ml. of concentrated hydrochloric acid is added, portionwise, 15.22 gm. (0.0564 mole) of 3,5-dinitro-4-chlorobenzotrifluoride. The mixture is warmed to 60°, stirred and allowed to cool to room temperature, then stirred at room temperature for five hours and allowed to stand overnight.

To this mixture is added slowly with cooling, a 50% solution of sodium hydroxide until the mixture is strongly basic. The insoluble material is removed by filtration, dissolved in water and washed well with methylene chloride. The filtrate is extracted with additional $CH_2Cl_2$. The methylene chloride extracts are dried over anhydrous $MgSO_4$ and the solvent removed. The combined solid is recrystallized from ethanol-water. There is obtained 9.02 gm. melting at 95°–6°.

b. Diethyl N,N'-[2-chloro-5-(trifluoromethyl)-m-phenylene)dioxamate

To a solution of 15.16 gm. (0.072 mole) of 4-chloro-3,5-diamino-α,α,α-trifluorotoluene in 100 ml. of dry ethyl acetate is added 18.22 gm. (0.18 mole) of triethylamine. The resulting solution is cooled to 0° in an ice-bath and to the stirred solution is added 24.5 gm. (0.18 mole) of ethyloxalyl chloride, keeping the temperature below 15°. The mixture is stirred in the ice-bath for one hour and then allowed to stand overnight at room temperature.

The precipitate is removed by filtration and washed with ethyl acetate. The precipitate is added to 500 ml. of water and the insoluble material is removed by filtration. There is obtained 12.39 gm. of material melting at 205°–207°.

The ethyl acetate filtrate is concentrated to dryness. There is obtained 14.8 gm. of material melting at 205°–7°.

Recrystallization of a sample from ethanol-water (2:1) gives material melting at 206°–7°.

Analysis Calc'd. for: $C_5H_{14}ClF_3N_2O_6$: C, 43.86; H, 3.43; Cl, 8.63; F, 13.87; N, 6.82. Found: C, 44.08; H, 3.48; Cl, 8.64; F, 13.59; N, 7.00.

c. Product

A solution of 5.00 gm (0.012 mole) of diethyl N,N'-[2-chloro-5-(trifluoromethyl)-m-phenylene] dioxamate in 200 ml. of methylene chloride is extracted with 35 ml. of 1N sodium hydroxide solution. The methylene chloride layer is washed once with water and this wash is added to the basic extract. The combined aqueous phase is acidified with dilute hydrochloric acid. The resulting precipitate is removed by filtration and washed with water. There is obtained 4.16 gm. (98%) of material melting at 210° (dec.). Recrystallization from water gives material melting at 213° (dec.).

Analysis Calc'd for: $C_{11}H_6ClF_3N_2O_6$: C, 37.25; H, 1.70; Cl, 10.00; F, 16.07; N, 7.90. Found: C, 36.72; H, 1.61; Cl, 10.37; F, 15.03; N, 7.79. The NMR spectra is in agreement.

EXAMPLE 10

N,N'-(4,6-Dichloro-m-phenylene)dioxamic acid a. 1,3-Diamino-4,6-dichlorobenzene

To a solution of 399 gm. (1.77 mole) of stannous chloride dihydrate in 975 ml. of concentrated hydrochloric acid is added 60 gm. (0.258 mole) of 1,5-dichloro-2,4-dinitrobenzene. The temperature rises to 72° and a solution occurs. The mixture is allowed to cool to room temperature and then cooled in an ice-bath (to 5°). A cold 50% solution of sodium hydroxide is added, with cooling, until the mixture is strongly basic. The mixture is filtered and the precipitate on the funnel washed four times with 500 ml. portions of ethyl acetate. The ethyl acetate extracts are combined, dried over anhydrous $M_9SO_4$ and the solvent removed. The residue is recrystallized from 50% ethanol-water. There is obtained 31.9 gm. (70%) of colorless needles melting at 142–3°.

b. Diethyl (4,6-dichloro-m-phenylene)dioxamate

To a solution of 31.9 gm. (0.18 mole) of 1,3-diamino-4,6-dichlorobenzene in 75 ml. of dry dimethylformamide is added 300 ml. of dry ethyl acetate and 43.6 gm. (0.432 mole) of triethylamine. The resulting solution is cooled to 0° in an ice-bath. To the stirred solution is added dropwise 59.0 gm. (0.432 mole) of ethyl oxalyl chloride, keeping the temperature below 15°. The mixture is stirred in the ice-bath for one hour and then allowed to stand at room temperature for 48 hours.

Most of the solvents are removed by distillation under reduced pressure. The residue is poured into 1 liter of cold water. The precipitate is removed by filtration and recrystallized from ethanol. There is obtained 55.3 gm. (81%) of long colorless needles melting at 124°–5°.

Analysis Calc'd. for: $C_{14}H_{14}Cl_2N_2O_6$: C, 44.58; H, 3.74; Cl, 18.80; N, 7.43. Found: C, 44.67; H, 3.75; Cl, 18.90; N, 7.74.

c. Product

A solution of 5.66 gm. (0.015 mole) diethyl N,N'-(4,6-dichloro-m-phenylene)dioxamate in 200 ml. of methylene chloride is extracted with 35 ml. of 1N sodium hydroxide solution. The methylene chloride layer is extracted with water. The combined aqueous extracts are acidified with dilute hydrochloric acid. The precipitate is removed by filtration, heated on the steam bath for ten minutes with water, the mixture allowed to cool and the precipitate removed by filtration. There is obtained 4.80 gm. (100%) of colorless gelatinous material melting above 340°.

Analysis Calc'd. for: $C_{10}H_6Cl_2N_2O_6$: Cl, 22.08; N, 8.73. Found: Cl, 22.18; N, 8.32. The infrared spectra is in agreement. Uv: λ max (0.1N NaOH) 235 (13,200) mμ.

EXAMPLE 11

N,N'-(5-Carboxy-2-methylphenylene-1.3-)dioxamic acid a. 3,5-diamino-p-toluic acid 3,5-dinitro-p-toluic acid (10.0 gm.) is dissolved in methanol (300 ml.) and 5% palledium on charcoal (1.0 gm.) added. Reduction is carried out in a Parr apparatus for one hour at 40 psi of hydrogen. The product precipitates and the reaction mixture warmed until solution is complete. The catalyst is removed by filtration, washed with a few cc of methanol and the filtrate cooled to 0°. The product precipitates in fine needles and is collected by filtration, washed with a few ml. of methanol and dried (5.95 gm., 81% yield, m.p. 218°–220° dec.). The thin layer chromatogram (Silica gel, 5% methanol in chloroform) shows the material to be homogeneous.

b. Diethyl N,N'-(5-Carboxy-2-methyl-phenylene-1,3)dioxamate

Ethyl oxalyl chloride (3.5 gm.) is added slowly at 0° to a solution of 3,5-diamino-p-toluic acid (2.0 gm.) in DMF (25 ml.) and triethylamine (2.5 gm.) with stirring. The reaction mixture is stirred for one hour at 0°m.p. then 18 hours at room temperature. Dilution with water (300 ml.) gives a cream colored solid that is collected by filtration, washed with water and dried. (2.2 gm., m.p. 232°–234°). Recrystallization from ethanol gives a white solid (1.85 gm., m. 234°–235°, 48% yield).

Analysis Calc'd. for: $C_{16}H_{18}O_8N_2$: C, 52.46; H, 4.95; N, 7.65. Found: C, 52.58; H, 4.97; N, 7.55.

c. Product

Dimethyl N,N'-(5-Carboxy-2-methyl-phenylene-1,3-)dioxamate (1.0 gm.) is stirred for three hours at room temperature in 1.0 N NaOH (15 ml.). The solution is then acidified with 3 N HCl to give the desired diacid as fine white needles (0.85gm.). Recrystallization from water gives a material that melted 230° (dec.) (0.70 gm. 83% yield).

Analysis Calc'd. for: $C_{12}H_{10}O_8N_2$: C, 46.46; H, 3.25; N, 9.03. Found: C, 42.06; H, 2.64; N, 8.75 (3.1% $H_2O$). uv ($H_2O$) λ max (ε) 231 (20.850) IR(Nujol): NH/OH 3470 (sh), 3360. acid OH 2600-2500, C=O 1700, C=C/amide 11 1585, 1515, C—O/C—N/-other 1300, 1235, 1195. (Sample appears amorphous.)

EXAMPLE 12

N,N'-(5-Carboxy-2-chlorophenylene-1,3-)dioxamic acid a. Methyl 4-chloro-3,5-dinitrobenzoate

4-Chloro-3,5-dinitrobenzoic acid (25.0 gm.) is dissolved in a cooled solution of methanol (125 ml.) and concentrated sulfuric acid (3.0 ml.). The reaction mixture is allowed to warm to room temperature and then heated to reflux for 18 hours. The product precipitated as light yellow needles on cooling, which are collected by filtration and washed with 15 ml. of methanol (24.0 gm., m.p. 102°–104.5°). Recrystallization from methanol gives light yellow needles (23.6 g., m.p. 104–105.5). 89% yield).

Analysis Calc'd. for: $C_7H_3N_2Cl$: C, 36.87; H, 1.93; N, 10.75; Cl, 13.61. Found: C, 36.51; H, 1.91; N, 10.86; Cl, 13.84.

b. Methyl 3,5-diamino-4-chlorobenzoate

Methyl 4-Chloro-1,5-dinitrobenzoate (9.0 gm.) is suspended in 50% ethanol (60 ml.). 14.5 gm. of electrolytically reduced iron powder is added and the stirred reaction mixture heated to reflux. Concentrated hydrochloric acid (1 ml.) in 5 ml. of 50% ethanol is added dropwise and refluxing continued for 1.5 hours. The reaction mixture is allowed to cool slightly and made basic (pH 8) with 20% NaOH. The iron is removed by filtration and the filtrate adjusted to pH 5 with 3N HCl and taken to dryness under reduced pressure, leaving a tan solid. Recrystallization from chloroform-Skellysolve "B" gives a material melting at 110°–120° (5.4 gm.). Recrystallization from chloroform gives tan needles (4.45 gm., m.p. 112°–125°, 64% yield).

Analysis calc'd. for: $C_8H_3O_2N_2Cl$: C, 47.89; H, 4.52; N, 13.97; Cl, 17.67. Found: C, 47.69; H, 4.51; N, 13.80; Cl, 17.67.

c. Diethyl N,N'-(5-carbomethoxy-2-chlorophenylene-1,3-)dioxanate

Ethyl oxalylchloride (6.6 gm.) is added slowly at 0° to a solution of methyl-4-chloro-3,5-diaminobenzoate (4.45 gm.) in DMF (50 ml.) and triethylamine (5.0 gm.) with stirring. The reaction mixture is stirred for one hour at 0°, then 18 hours at room temperature. Dilution with water (450 ml.) gives a cream colored solid that is collected by filtration, washed with water and dried. Recrystallized from acetone gives white needles (4.45 gm., m.p. 203.5°–204.5°, 50% yield).

Analysis Calc'd. for: $C_{16}H_{17}O_8N_2Cl$: C, 47.95; H, 4.28; N, 6.99; Cl, 8.95. Found: C, 47.45; H, 4.26; N, 6.95; Cl, 8.94.

d. Product

Diethyl N,N'-(5-carbomethoxy-2-chlorophenylene-1,3-)dioxamate is dissolved in 1.0N NaOH (12 ml.) with stirring. The sodium salt precipitates after 30 minutes and is collected by filtration. The solid is dissolved in water (15 ml.) and added to the filtrate. The clear solution is acidified with 3N HCl. The desired diacid precipitates as a white solid that is collected by filtration, washed with a few ml. of water and dried (0.775 gm., 94% yield, m.p.>320°).

Analysis Calc'd. for: $C_{11}H_7O_6N_2Cl$: C, 39.95; H, 2.14; N, 8.47; Cl, 10.72. Found: C, 36.57; H, 2.19; N, 7.67; Cl, 8.55. Corrected for 9.49% $H_2O$.

EXAMPLE 13

N,N'-(2-carboxyphenylene-1,3-)dioxamic acid a. Methyl 2,6-dinitrobenzoate

1-Methyl-3-p-tolyltriazene (1.64 gm.) in ether (15 ml.) is added dropwise at 0° to 2,6-dinitrobenzoic acid (2.1 gm.) in ether (25 ml.) with stirring. Stirring at 0° is continued for one hour, then at room temperature for one hour. The reaction mixture is diluted with ether (200 ml.) and extracted with 1N HCl, then with saturated $Na_2CO_3$. Removal of the ether gave a solid which crystallized from methanol (1.40 gm., m.p. 150°–151.5°, 62.5% yield).

Analysis Calc'd. for: $C_8H_6O_6N_2$: C, 42.49; H, 2.67; N, 12.39. Found: C, 42.55, H, 2.74, N, 12.10.

b. Methyl 2,6-diaminobenzoate

Methyl 2,6-dinitrobenzoate (15.0 gm.) is suspended in methanol (500 ml.) and 5% palladium on charcoal (1.5 gm.) added. Reduction is carried out on a Parr apparatus for two hours. The solution is filtered with suction and the catalyst washed with a few ml. of methanol. Removal of the methanol gives a brown crystalline product. Extraction with chloroform (50 ml.) and treatment with Darco® gives the product (10.9 gm. 96% yield, m.p. 78°–79.5°). The thin layer chromatogram (Silica gel, 3% methanol in chloroform) shows the material to be homogeneous.

c. Diethyl N,N'-(2-Carbomethoxyphenylene-1,3-)dioxamate

Ethyl oxalyl chloride (9.0 gm.) is added slowly at 0° to a solution of methyl-2,6-diaminobenzoate (5.0 gm.) in DMF (35 ml.) and triethylamine (7.0 gm.) with stirring. The reaction mixture is stirred for one hour at 0°, then 18 hours at room temperature. Dilution with water (450 ml.) gives a yellow solid that is collected by filtration, washed with water and dried. Recrystallization from methanol (200 ml.) gives a white product (7.45 gm., m.p. 156–167.5, 68% yield).

Analysis Calc'd. for: $C_{16}H_{18}O_8N_2$: C, 52.46; H, 4.95; N, 7.65. Found: C, 52.13; H, 4.77; N, 7.63.

d. Product

Diethyl N,N'-(2-carbomethoxyphenylene-1,3-)dioxamate (1.0 gm.) is stirred for one hour at room temperature in 1.0 N NaOH (20 ml.). The sodium salt is collected by filtration and dissolved in water (25 ml.). This solution is added to the filtrate, then the clear solution acidified with 3N HCl to give the desired diacid as a white solid (0.83 gm., 102% yield. Analysis shows 7.43% $H_2O$, m.p. >310°).

Analysis Calc'd. for: $C_{11}H_8O_8N_2$: C, 44.60; H, 2.72; N, 9.46. Found (Corrected for 7.43% $H_2O$): C, 40.29; H, 2.38; N, 8.40. IR(Nujol): NH/OH 3610, 3520, 3440, 3260 acid OH 2460, C=O 1700, C=C/Amide II 1590, 1523, C—O/O—N/-other 1325, 1295, 1265, 1210, 1185.

EXAMPLE 14

N,N'-(5-Methoxyphenylene-1,3-)dioxamic acid a. 3,5-Diaminoanisole 3.5-Dinitroanisole (20 gm.) is suspended in methanol (250 ml.) and 5% palladium on charcoal (2.0 gm.) added. Reduction is carried out in a Parr apparatus for one hour. The solution is filtered with suction and the catalyst washed with a few cc of methanol. Removal of the methanol gives a clear brown glass which crystallized on standing. Extraction with boiling benzene (250 ml.) and treatment with Darco® gives white needles (8.7 gm., m.p. 79–80°, 63% yield).

Analysis Calc'd. for: $C_7H_{10}ON_2$: C, 60.85; H, 7.30; N, 20.28. Found: C, 61.21; H, 7.34; N, 20.29.

b. Diethyl N,N'-(5-Methoxyphenylene-1,3-)dioxamate

Ethyl oxalyl chloride (9.0 gm.) is added slowly at 0° to a solution of 3,5-diaminoanisole (4.15 gm.) in DMF (35 ml.) and triethylamine (6.5 gm.) with stirring. The reaction mixture is stirred for one hour at 0°, then 18 hours at room temperature. Dilution with water (400 ml.) gives a light yellow product that is collected by filtration, washed with water and dried. Recrystallization from methanol gives a light yellow product (9.5 gm., m.p. 172–173, 93% yield).

Analysis Calc'd. for: $C_{15}H_{18}O_7N_3$: C, 53.25; H, 5.36; N, 8.28. Found: C, 53.09; H, 5.35; N, 8.19.

c. Product

Diethyl N,N'-(5-methoxyphenylene-1,3-)dioxamate (2.0 gm.) is stirred at room temperature in 1.0 N NaOH (15 ml.). The sodium salt precipitates out in a white mass. Water (15 ml.) is added and stirring continued for thirty minutes. The reaction mixture is filtered and the white precipitate dissolved in water (15 ml.) and combined with the filtrate. The clear solution is then acidified with 3 N HCl to give the desired diacid as an off-white solid (0.86 gm., m.p. >325°, 52% yield). Recrystallization from water gives fine needles, which melt above 325°.

u.v. ($H_2O$) λmax (ε): 252 (14,550). IR(Nujol): NH/OH 3600, 3480, 3440, 3330, acid OH and/or bonded NH/OH 2450 (broad C=O 1720, C=O/C=C=C=N or amide, 1620, 1565, 1545, C—O/C—N/-other 3215, 1270, 1220, 1170, 1070. (IR noted water in sample).

EXAMPLE 15

N,N'-(2-Chloro-5-methylphenylene-1,3-)dioxamic acid a. 3,5-Diamino-4-chlorotoluene 4-chloro-3,5-dinitrotoluene (9.0 gm.) is dissolved in 50% ethanol (30 ml.). Electrolytically reduced iron powder (14.2 gm.) is added and the stirred reaction mixture heated to reflux. Concentrated HCl (1 ml.) in 50% ethanol (5 ml.) is added dropwise and refluxing continued for one hour. The reaction mixture is allowed to cool slightly and made basic (pH 8) with 20% NaOH, then the iron removed by filtration. The filtrate is taken to dryness under reduced pressure and the residue extracted with hot Skellysolve "B" (700 ml.). The product precipitates in long needles that were collected by filtration (4.57 gm., m.p. 114°–115.5°, 70% yield).

Analysis Calc'd. for: $C_7H_3N_2Cl$: C, 53.71; H, 5.79; N, 17.90; Cl, 22.66. Found: C, 53.82; H, 5.76; N, 18.27; Cl, 22.70.

b. Diethyl N,N'-(2-chloro-5-methylphenylene-1,3-)dioxamate

Ethyl oxalyl chloride (9.5 gm.) is added slowly at 0° to a solution of 3,5-diamino-4-chlorotoluene in DMF (35 ml.) and triethylamine (7.0 gm.). The reaction mixture is stirred for one hour at 0°, then 18 hours at room temperature. Dilution with water (500 ml.) gives a light yellow solid which is collected by filtration, washed with water and dried. Recrystallization from acetone gives fine white needles (8.27 gm., m.p. 180–181.5, 71% yield).

Analysis Calc'd. for: $C_{15}H_{17}O_6N_2Cl$: C, 50.49; H, 4.80; N, 7.85; Cl, 9.94. Found: C, 50.86; H, 4.90; N, 7.90; Cl, 10.02.

c. Product

Diethyl N,N'-(2-chloro-5-methylphenylene-1,3-)dioxamate (1.0 gm.) is stirred at room temperature in 1.0 N NaOH (20 ml.). The sodium salt precipitates out as a white mass and is filtered, dissolved in water (50 ml.) and combined with the filtrate. The clear solution is then acidified with 3 N HCl to give the desired diacid as a white solid. Recrystallization from water gives fine cotton-like needles (0.44 gm., m.p. 200°–202° (dec.), 52% yield).

Analysis Calc'd. for: $C_{11}H_9O_6N_2Cl$: C, 43.94; H, 3.02; N, 9.32; Cl, 11.79. Found: (Corrected for 6.89 $H_2O$) C, 44.08; H, 2.58; N, 9.39; Cl, 11.79. u.v. ($H_2O$) λ max (ε): 196 (9,750) 215 (sh) (3,150) 245 (12,550) IR(Nujol): NH 3380, 3340, NH/acid OH 3140, 2590 C=O 1795, 1755, C=O 1735, 1700, C=C/amide II 1600, 1560, 1525, C—O/other 1250, 1195, 1055, 865, 735.

EXAMPLE 16

4-Butyl-N,N'-(m-phenylene)dioxamic acid a. Diethyl 4-butyl-N,N'-(m-phenylene)dioxamate 2,4-Dinitrobutylbenzene (10 gm., 0.045 mole in methanol (200 ml.) is treated with hydrogen (40 psi) in the presence of 5% palladium on charcoal (1.0 gm.) on a Parr hydrogenator until hydrogen uptake stopped (ca. 2 hrs.). The catalyst is removed by filtration and the solvent removed from the filtrate to leave a red oil. The crude red oil is used in the subsequent reaction without further purification.

A mixture of the red oil above and diethyl oxalate (100 ml.) is heated at reflux for two hours. The solvent is removed from the reaction mixture to leave an oil. The oil is chromatographed on silica gel with methylene chloride as the eluent. The major component is isolated as an oil, but is crystallized from methanol-water to give a white solid (m.p. 110°, 4.3 gm.).

Analysis Calc'd. for: $C_{18}H_{24}O_6N_2$: C, 59.33; H, 6.64; N, 7.69. Found: C, 59.18; H, 6.51; N, 8.10.

b. Product

Diethyl 4-butyl-N,N'-(m-phenylene)dioxamate (1.0 gm., 2.74 mmoles) is stirred at room temperature in 1.0 N NaOH (10 ml.) until the solution is complete. The solution is adjusted to pH 3 and the resulting white solid collected (0.5 gm., mp 232°).

EXAMPLE 17

4-Methoxy-N,N'-(m-phenylene)dioxamic acid a. Diethyl 4-Methoxy-N,N'-(m-phenylene)dioxamate 2,4-Diaminoanisole (5.0 gm., 0.036 mole) is dissolved in dimethylformamide (100 ml.) with triethylamine (8.0 gm., 0.079 mole). Ethyl oxalylchloride (10 gm., 0.073 mole) is added carefully to the colled reaction mixture. The reaction mixture is stirred at room temperature for 24 hours. The reaction mixture is poured innto water (500 ml.) and the solid collected by filtration (11.75 gm.). Recrystallization from ethanol and treatment with Darco® gives an off-white solid (6.70 gm., 55%, m.p. 140°–145°).

Analysis Calc'd. for: $C_{15}H_{18}O_7N_2$: C, 53.27; H, 5.36; N, 8.25. Found: C, 53.72; H, 5.48; N, 8.11.

b. Product

Diethyl 4-methoxy-N,N'-(m-phenylene)dioxamate (1.0 gm., 0.0029 mole) is stirred in 1.0 N NaOH (10 ml.) at room temperature for one hour, then heated at reflux for thirty minutes. The reaction mixture is diluted with water (25 ml.) and the pH adjusted to 3 with hydrochloric acid. The resulting solid is collected and washed with acetone (0.72 gm., 86%, m.p. >320°).

uv(Etoh) λ (ε): 222 (8,900), 241 sh(8,100), 278 (13,900, 305 sh (11,550). ir (Nujol): NH 3370, 3340; C=O 1730, 1705; C=C/amide II 1605, 1535, 1495; aromatic CH 8:5.

EXAMPLE 18

N,N'-(5-Acetyl-b 2-chloro-m-phenylene)dioxamic acid a. 4-Chloro-3,5-dinitrobenzoyl chloride A mixture of 75.75 gm. (0.307 mole) of 4-chloro-3,5-dinitrobenzoic acid and 64.0 gm. (0.307 mole) of phosphorus pentachloride is heated at reflux for ninety minutes and cooled to room temperature. The phosphorus oxychloride is removed by distillation in vacuo. The residue is washed with Skellysolve "B" and the solvent removed by decantation. The oily residue is recrystallized from benzene-cyclohexane. There is obtained 58.2 gm (72%) of tan needles melting at 55°–57°.

b. 4-Chloro-3,5-dinitroacetophenone

A mixture of 8.76 gm. of magnesium turnings, 80 ml. of absolute ethanol and 2 ml. of carbon tetrachloride is stirred and to the mixture is added 25 ml. of chloroform. The mixture is refluxed for one hour. To the solution is added a solution containing 54.5 gm. of diethyl malonate in 53 ml. of chloroform. The solution is refluxed for three hours and allowed to cool to room temperature. The solution is evaporated to dryness in vacuo. The oily residue is dissolved in 62 ml. of chloroform and to the solution is added a solution containing 58.2 gm. (0.22 mole) of 4-chloro-3,5-dinitrobenzoyl chloride in 55 ml. of chloroform. The reaction mixture is stirred at room temperature for twelve hours. The solution is warmed in a water-bath at 33°–36° for one hour and allowed to cool to 5° in an ice bath. To the solution is added, slowly, 111 ml. of 21.5% sulfuric acid.

An additional 70 ml. of water is added to obtain a clear solution. The chloroform phase is separated from the aqueous and evaporated to dryness in vacuo.

To the oily residue is added, 45 ml. of water, 67 ml. of glacial acetic acid, 8.3 ml. of concentrated sulfuric acid and the mixture refluxed for eight hours. The solution is cooled to room temperature and evaporated to dryness in vacuo. The tan residue is triturated with ice-water and the pH adjusted to 7.0 with sodium bicarbonate. The precipitate is removed by filtration. The solid residue is recrystallized from ethanol to yield 30.7 gm., (57%) of fine tan needles melting at 86°–89°. One gram of this material is recrystallized from ethanol. The melting point is 88°–89°.

Analysis Calc'd. for: $C_8H_5N_2ClO_5$: C, 39.28; H, 2.06; N, 11.45; Cl, 14.50% Found: C, 39.06; H, 2.20; N, 11.25; Cl, 14.51%.

c. 4-Chloro-3,5-diaminoacetophenone

To a stirred solution of 185 gm. of stannous chloride dihydrate in 450 ml. of concentrated hydrochloric acid is added 28.2 gm. (0.115 mole) of 4-chloro-3,5-dinitroacetophenone. The exothermic reaction causes the temperature to rise to 78°. The solution is cooled to room temperature over a period of two hours. The solution is cooled to 5° in an ice-bath and there is added 50% sodium hydroxide slowly until the mixture is strongly basic. The precipitate is removed by filtration. The precipitate is slurried several times with hot ethylacetate and filtered. The combined extracts are added to the aqueous filtrate and shaken for ten minutes. The phases are separated.

The organic phase is dried over magnesium sulfate. The drying aget is removed by filtration. The filtrate is evaporated to dryness in vacuo. The solid residue is recrystallized from methanol. There is obtained 14.85 gm. of yellow needles melting at 125°–127°. The filtrate is evaporated to dryness in vacuo. There is obtained 4.25 gm. of yellow needles melting at 123°–126°. The total yield is 90%.

Recrystallization from methanol gives material melting at 123°–6°.

Analysis Calc'd. for: $C_8H_9N_2ClO$: C, 52.04; H, 4.91; N, 15.17; Cl, 19.20%. Found: C, 52.21; H, 4.93; N, 15.05; Cl, 19.22%.

d. Diethyl N,N'-(5-acetyl-2-chloro-m-phenylene)dioxamate

A solution of 13.80 gm. (0.07 mole) of 4-chloro-3,5-diaminoacetophenone in 250 ml. of ethyl acetate and 17.0 gm. (0.168 mole) of triethylamine is cooled to 0° in an ice bath. To the solution is added, dropwise, 22.9 gm. (0.168 mole) of ethyl oxalyl chloride. The temperature is kept below 15° and the mixture stirred in an ice bath for one hour. The mixture is warmed to room temperature over a period of eighteen hours.

The precipitate is removed by filtration. The precipitate is stirred in one liter of water and the insoluble material removed. The insoluble material is recrystallized from ethanol to yield 17.5 gm. of white needles melting at 183°-184°. The organic filtrate (ethyl acetate) is evaporated to dryness and recrystallized from ethanol to yield 4.63 gm. of white needles melting at 182°-184°. The total yield is 98%.

Analysis Calc'd. for: $C_{16}H_{17}N_2ClO$—: C, 49.94; H, 4.45; N, 7.28; Cl, 9.21. Found: C, 49.92; H, 4.57; N, 7.10; Cl, 9.30.

e. Product

A solution of 11.54 gm. (0.03 mole) of diethyl N,N'-(5-acetyl-2-chloro-m-phenylene)dioxamate in 216 ml. of 0.31 N NaOH is stirred. The aqueous solution is extracted with methylene chloride. The aqueous phase is separated and acidified with dilute hydrochloric acid. The precipitate is removed by filtration and washed with water. There is obtained 9.88 gm. (100%) of a white solid melting at 208° (dec.). A sample recrystallized from water possesses the same melting point.

Analysis Calc'd. for: $C_{12}H_9N_2ClO_7$: C, 42.73; H, 3.29; N, 8.31; Cl, 10.51%. Found: C, 42.38; H, 2.99; N, 8.26; Cl, 10.65%. uv $\lambda$ max 0.1 N NaOH: 250 (19,750) 315 sh. (2,250)m$\mu$. IR: 3480, 3360, 3330, 3100 (NH/OH), 2600 (acid OH), 1705 (C=O), 1595, 1510 (C=C/amide II), cm$^{-1}$ NMR (DMSO-D$_6$) S10.43 (S,2,NH), S8.27 (S,2,aromatic), S2.55 (S,3,CH$_3$).

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula I. The preferred method of administration is by inhalation into the lung by means of an aerosol liquid or powder for insufflation.

For oral administration, either solid or fluid unit dosage forms can be prepared. For preparing solid compositions such as tablets, the compound of Formula I is mixed with conventional ingredients such as talc. magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent ad filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying via of water for injection is supplied to reconstitute the liquid prior to use. Perenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 gm.

The preferred compositions are those adapted or inhalation into the lung and containing a compound of the invention which is water-soluble. For treatment of allergic conditions of the nose, such as rhinitis, compositions adapted for contact with nasal linings are preferred.

Compositions for inhalation are of three basic types: (1) a powder mixture preferably micropulverized with particle size preferably from about 1 to about 5 microns; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.001 to about 10 mg. of compound in a single dose, administered parenterally or by inhalation in the compositions of this invention, are effective for preventing allergy attacks. More specifically, the single dose is from about 0.05 to about 10 mg. of compound. The oral and rectal dose is from about 0.5 to about 30 mg. in a single dose. More specifically, the single dose is from about 1 to about 20 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual insufflates 0.2 mg. of the tris(hydroxymethyl)aminomethane salt of N,N'-(5-cyano-m-phenylene)dioxamic acid. Four hours later the individual insufflates 0.002 mg. of the same compound and every four to six hours thereafter insufflates 0.002 mg. of the same compound until effective asthma propylaxis is not provided. The individual then insufflates 0.2 mg. of the same compound, the reduces the insufflation dosage to 0.002 mg. four to six hours later. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions when administered to a sensitized individual prior to the time that the individual comes into contact with substances (antigens) to which he is allergic, will prevent the allergic reaction with would otherwise occur.

For example, the process can be used for prophylactic treatment of such chronic conditions as bronchial asthma, allergic rhinitis, food allergy, hay fever, urticaria, auto-immune diseases, exercise induced asthma, stress induced asthma, systemic anaphylaxis, and bird fancier's disease.

EXAMPLE 19

A lot of 10,000 tablets, each containing 2 mg. of N,N'-(5-cyano-m-phenylene)dioxamic acid is prepared from the following types and amounts of ingredients:

| | |
|---|---|
| N,N'-(5-cyano-m-phenylene)-dioxamic acid, micronized | 20 Gm. |
| Dicalcium phosphate | 1,000 Gm. |
| Methylcellulose, U.S.P. (15 cps) | 60 Gm. |
| Talc | 150 Gm. |
| Corn Starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of 1 tablet every four to six hours.

EXAMPLE 20

One thousand two-piece hard gelatin capsules, each containing 1.0 mg. of N,N'-(2-chloro-5-cyano-m-phenylene)dioxamic acid are prepared from the following types and aounts of ingredients:

| | |
|---|---|
| N,N'-(2-Chloro-5-cyano-m-phenylene)-dioxamic acid | 1 Gm. |
| Talc | 150 Gm. |
| Magnesium stearate | 1 Gm. |

The ingredients are mixed well and filled into capsules of the proper size.

Capsules so prepared are useful in preventing attacks of bronchial asthma at a dose of one capsule every four to six hours.

EXAMPLE 21

One thousand tablets, each containing 6 mg. of N,N'-(2-chloro-m-phenylene)dioxamic acid are prepared from the following types and amounts of ingredients:

| | |
|---|---|
| N,N'-(2-chloro-m-phenylene)- | |

| | |
|---|---|
| dioxamic acid | 6 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of 1 tablet before meals.

EXAMPLE 22

One thousand tablets, each containing 0.5 mg. of N,N'-(2-chloro-5-cyano-m-phenylene)dioxamic acid are prepared from the following types and amounts of ingredients:

| | |
|---|---|
| N,N'-(2-Chloro-5-cyano-m-phenylene)-dioxamic acid | 0.5 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of 1 tablet before meals.

EXAMPLE 23

A sterile preparation suitable for intramuscular injection and containing 0.2 mg. of N,N'(2-chloro-m-phenylene)dioxamic acid in each milliliter is prepared from the following ingredients:

| | |
|---|---|
| N,N'-(2-Chloro-m-phenylene)-dioxamic acid | 0.2 Gm. |
| Benzyl benzoate | 200 ml. |
| Methylparaben | 1.5 Gm. |
| Propylparaben | 0.5 Gm. |
| Cottonseed oil c.s. | 1,000 ml. |

One milliliter of this sterile preparation is injected for prophylactic treatment of allergic rhinitis

EXAMPLE 24

Six hundred ml. of an aqueous solution containing 2.0 mg. of the tris(hydroxymethyl)aminomethane THAM salt of N,N'-15-cyano-m-phenylene dioxamic acid per ml. is prepared as follows:

| | |
|---|---|
| Tris(hydroxymethyl)aminomethane (THAM) salt of N,N'-(5-cyano-m-phenylene)dioxamic acid | 1.2 Gm. |
| Sodium chloride | 5 Gm. |
| water for injection c.s. | 600 ml. |

The THAM salt and sodium chloride are dissolved in sufficient water to make 600 ml. and sterile filtered.

The solution is placed in nebulizers designed to deliver 0.25 ml. of solution per spray.

The solution is inhaled into the lungs every four to six hours for prevention of asthmatic attacks.

EXAMPLE 25

Six hundred ml. of an aqueous solution containing 0.2 mg. of the tris(hydroxymethyl)aminomethane THAM salt of N,N'-2-chloro-5-cyano-m-phenylene dioxamic acid per ml. is prepared as follows:

| | |
|---|---|
| Tris(hydroxymethyl)aminomethane (THAM) salt of N,N'-(2-chloro-5-cyano-m-phenylene)dioxamic acid | 0.12 Gm. |
| Sodium chloride | 5 Gm. |
| Water for injection q.s. | 600 ml. | the THAM salt and sodium chloride are dissolved in sufficient water to make 600 ml. and sterile filtered.

The solution is placed in nebulizers designed to deliver 0.25 ml of solution per spray.

The solution is inhaled into the lungs every four to six hours for prevention of asthmatic attacks.

EXAMPLE 26

A powder mixture consisting of 0.005 gram of tris(hydroxymethyl)aminomethane salt of N,N'-(5-cyano-m-phenylene) dioxamic acid and sufficient lactose to make 5 grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 27

A powder mixture consisting of 0.002 gram of tris(hydroxymethyl)aminomethane salt of N,N'-(2-chloro-5-cyano-m-phenylene)dioxamic acid and sufficient lactose to make 5 grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 28

Twelve grams of an aerosol composition are prepared from the following ingredients:

| | |
|---|---|
| Tris hydroxymethyl aminomethane salt of N,N'-(5-cyano-m-phenylene)dioxamic acid | 0.025 Gm. |
| Freon 12 | 1.440 Gm. |
| Freon 114 | 2.160 Gm. |
| Water | 7.775 Gm. |
| Sorbitan monoleate | 0.600 Gm. |

The THAM salt is dissolved in the water and chilled to −30° C. and added to the chilled Freons. The twelve grams of compositions are added to a 13 cc. plastic coated bottle and capped with a metering valve. The metering valve releases 80 mg. of composition in an aerosol. The aerosol is inhaled every four to six hours for prevention of asthmatic attacks.

EXAMPLE 29

In individuals who require continual treatment in the Examples 19 through 28, the dosage of the Example is given initially and each succeeding administration of the drug is at 1/50 of the initial dosage. This maintenance dosing is continued until effective allergy prophylaxis is not obtained. The initial dosage of Examples 19 through 28 is then started once more, followed by the maintenance dosages.

EXAMPLE 30

After allowing for the differing solubilities of the compounds and the activity of the particular compound as measured, for example, by the in vivo rat passive cutaneous anaphylaxis assay, a suitable quantity of each of the compounds of Table I through Table VII and Examples 1–18, is substituted for the active compound in the compositions and uses of Examples 19 through 28. Results showing anti-allergy activity are obtained.

EXAMPLE 31

The rat passive cutaneous anaphylaxis assay is run in the following manner:

Female Spraque-Dawley 250 gm. rats are skin-sensitized with rat anti-ovalbumin homocytotropic antibody that is heat labile and has a passive cutaneous anaphylaxis titer of 1:128. After a 72-hour latency period, the animals are challenged i.v. with 4 mg. ovalbumin (OA)+5 mg. Evans blue dye and the test compound. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

The tris(hydroxymethyl)aminomethane salt of N,N'-(5-cyano-m-phenylenediamine)dioxamic acid is prepared by dissolving the dicarboxylic acid in an equivalent weight of aqueous tris(hydroxymethyl)aminomethane and is tested in the rat passive cutaneous anaphylaxis assay in the above manner.

The inhibitory dose$_{20}$ for the tris(hydroxymethyl)aminomethane salt of N,N'(2-chloro-5-cyano-m-phenylene)dioxamic acid is 0.001 mg./kg. by the intravenous route.

Tables IV through VII are not rendered in the same manner as Tables I and II. However, the same illustrative scoping is intended.

N,N'-(2-chloro-5-cyano-m-phenylene)dioxamic acid is the most preferred oral medicament of this invention and is preferably administered as the diTHAM salt. This salt is readily prepared in the following manner:

To a hot solution of 0.3116 gm. (0.001 mole) of N,N'-(2-chloro-5-cyano-m-phenylene)dioxamic acid in 25 ml. of methanol if added a hot solution of 202.3 gm. (0.002 mole) of tris-(hydroxymethyl)aminomethane in 30 ml. of methanol. The mixture is stirred thoroughly and allowed to cool overnight in the refrigerator. The precipitate is removed by filtration. The filtrate is evaporated to dryness and the residue boiled with 15 ml. of methanol and the mixture allowed to cool in the refrigerator. The precipitate is removed by filtration and combined with the previous precipitate. There is recovered 0.400 gm. (70.5%) of a colorless solid melting at 204°–6° (dec.).

Analysis calcd. for: $C_{11}H_6ClN_3O_6$: C, 41.20; H, 5.09; Cl, 6.40; N 12.64%. Found: C, 41.30; H. 5.07, Cl, 6.52; N, 12.60%.

In Example 22, the diTHAM salt of N,N'-(2-chloro-5-cyano-m-phenylene)dioxamic acid can be used in place of the N,N'-(2-chloro-5-cyano-m-phenylene)dioxamic acid.

It should be noted that: in all the compositions and treatment examples of this patent application, the quantity of drug employed refers to the acid form rather than the weight of the acid plus the cation in this case the di-tris(hydroxymethyl)aminomethane.

A further subgenus of this invention is where X and W are hydrogen.

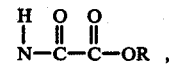

is located at the 5 position, Y is 5-acetyl. Z is at the 2 position and is selected from the group consisting of hydrogen, chloro, bromo, fluoro, alkyl of one to three carbon atoms, inclusive, and alkoxy of one to three carbon atoms, inclusive.

We claim:

1. A compound of the formula

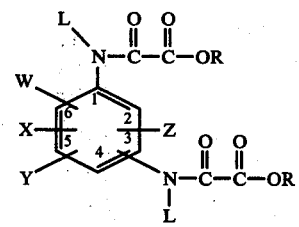

wherein W is hydrogen, X, Y, and Z can be the same or different and are selected from the group consisting of hydrogen, alkyl from one to six carbon atoms, inclusive, phenyl, alkoxy with the alkyl group having from one to six carbon atoms, inclusive, hydroxy, nitro, halogen, trifluoromethyl, and

wherein Q is selected from OD

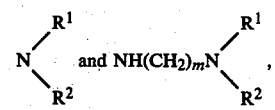

wherein D is hydrogen, or a pharmaceutically acceptable metal or amine cation wih the proviso that
when Q is OD, then D is the same R, M is 2 or 3, $R^1$ and $R^2$ are the same or different and are selected from the group consisting of hydrogen, alkyl from one to three carbon atoms, inclusive, and with the additional overall proviso that at least one of X, Y, and Z is not hydrogen when L is hydrogen;

L is selected from the group consisting of hydrogen, alkyl of from one to six carbon atoms, inclusive, benzyl, and monosubsubstituted benzyl wherein the substitutent is selected from the group consisting of alkyl from one to four carbon atoms, inclusive, and halogen;

the

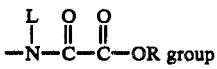

is located at the 3 or 4 position;
R is hydrogen, or a pharmaceutically acceptable metal or amine cation.

2. Compounds in accordance with claim 1 wherein X is hydrogen.

3. Compounds in accordance with claim 1 wherein X and Y are hydrogen.

4. Compounds in accordance with claim 1 wherein X, Y, and Z are the same or different and are selected from the group consisting of hydrogen, alkyl from one to three carbon atoms, inclusive, alkoxy with the alkyl group having from one to three carbon atoms, inclusive, hydroxy, nitro, halogen, trifluoromethyl, and

R is hydrogen or a pharmaceutically acceptable metal or amine cation.

5. Compounds in accordance with claim 4 wherein X is hydrogen.

6. Compounds in accordance with claim 4 wherein X and Y are hydrogen.

7. Compounds in accordance with claim 5 wherein Y and Z are the same or different and are selected from the group consisting of hydrogen, alkyl from one to three carbon atoms, inclusive, alkoxy with the alkyl group having from one to three carbon atoms, inclusive, nitro, fluoro, chloro, trifluoromethyl, and

and
L is selected from the group consisting of hydrogen and alkyl from one to three carbon atoms, inclusive.

8. Compounds in accordance with claim 7 wherein W and Y are hydrogen.

9. Compounds in accordance with claim 7 wherein Y and Z are the same or different and are selected from the group consisting of hydrogen, alkyl of from one to three carbon atoms, alkoxy with alkyl having from one to three carbon atoms, inclusive, fluoro, chloro, trifluoromethyl,

L is hydrogen;
R is hydrogen, or a pharmaceutically acceptable metal or amine cation.

10. Compounds in accordance with claim 9 wherein Y and Z are at the 2 and 5 position and

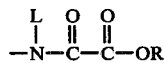

is at the 3 position.

11. Compounds in accordance with claim 10 wherein X and Y are hydrogen and Z is at the 5 position.

12. N,N'-(5-carboxy-m-phenylene)dioxamic acid according to claim 1.

13. N,N'-(2-chloro-m-phenylene)dioxamic acid according to claim 1.

14. Compounds in accordance with claim 10 wherein Y is hydrogen and Z is 5 carbamoyl.

15. (5-Carbamoyl-m-phenylene)dioxamic acid hydrate and its di-tris(hydroxymethyl)aminomethane salt according to claim 1.

16. Compounds in accordance with claim 10 wherein Y is 2-chloro and Z is 5-trifluoromethyl.

17. N,N'-[2-Chloro-5-(trifluoromethyl)-m-phenylene]dioxamic acid and its di-tris(hydroxymethyl)aminomethane salt according to claim 1.

18. Compounds in accordance with claim 9 wherein Y is 4-chloro and Z is 6-chloro and

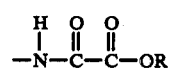

is at the 3 position.

19. N,N'-(4,6-Dichloro-m-phenylene)dioxamic acid and its di-tris(hydroxymethyl)aminomethane salt according to claim 1.

20. Compounds in accordance with claim 10 wherein Y is 2-methyl and Z is 5-carboxy.

21. N,N'-(5-Carboxy-2-methylphenylene-1,3-)dioxamic acid and its di-tris(hydroxymethyl)aminomethane salt according to claim 1.

22. Compounds in accordance with claim 10 wherein Y is 2-chloro and Z is 5-carboxy.

23. N,N'-(5-Carboxy-2-chlorophenylene-1,3-)dioxamic acid and its di-tris(hydroxymethyl)aminomethane salt according to claim 1.

24. Compounds in accordance with claim 9 wherein

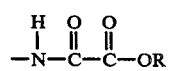

is at the 3 position, Y is hydrogen and Z is 2-carboxy.

25. N,N'-(2-Carboxyphenylene-1,3-)dioxamic acid and its di-tris(hydroxymethyl)aminomethane salt according to claim 1.

26. Compounds in accordance with claim 11 wherein Z is methoxy.

27. N,N'-(5-Methoxyphenylene-1,3-)dioxamic acid are its di-tris(hydroxymethyl)aminomethane salt according to claim 1.

28. Compounds in accordance with claim 10 wherein Y is 2-chloro and Z is 5-methyl.

29. N,N'-(2-Chloro-5-methylphenylene-1,3-)dioxamic acid and its di-tris(hydroxymethyl)aminomethane salt according to claim 1.

30. Compounds in accordance with claim 9 wherein

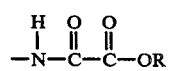

is at the 3 position, Y is hydrogen, and Z is 4-butyl.

31. 4-Butyl-N,N'-(m-phenylene)dioxamic acid and its di-tris(hydroxymethyl)aminomethane salt according to claim 1.

32. Compounds in accordance with claim 9 wherein

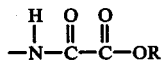

is at the 3 position, Y is hydrogen, and Z is 4:methoxy.

33. 4-Methoxy-N,N'-(m-phenylene)dioxamic acid and its di-tris(hydroxymethyl)aminomethane salt according to claim 1.

34. Compounds of the formula wherein
R is hydrogen, or a pharmaceutically acceptable metal or amine cation;
Z is selected from the group consisting of hydrogen, alkyl of from one to three carbon atoms, inclusive, alkoxy of from one to three carbon atoms, inclusive, fluoro, chloro, and bromo.

35. N,N'-(5-Acetyl-2-chloro-m-phenylene)dioxamic acid and its di-tris(hydroxymethyl)aminomethane salt according to claim 1.

* * * * *

UNITED STATES PATENT AND TRADEMARK OFFICE
CERTIFICATE OF CORRECTION

PATENT NO. : 4,159,278
DATED : June 26, 1979
INVENTOR(S) : Charles M. Hall, John B. Wright It is certified that error appears in the above—identified patent and that said Letters Patent is hereby corrected as shown below:

Column 35, lines 46 and 47, "W and Y are hydrogen" should read "Y is hydrogen".

Column 36, line 51, the first word "are" should read "and".

Signed and Sealed this

Fifteenth Day of June 1982

[SEAL]

Attest:

Attesting Officer

GERALD J. MOSSINGHOFF
Commissioner of Patents and Trademarks